(12) United States Patent
Baileykobayashi et al.

(10) Patent No.: US 11,927,589 B2
(45) Date of Patent: Mar. 12, 2024

(54) CARRIER PEPTIDE FRAGMENT FOR NUCLEOLAR LOCALIZATION AND USE THEREOF

(71) Applicant: TOAGOSEI CO., LTD., Tokyo (JP)

(72) Inventors: Nahoko Baileykobayashi, Tsukuba (JP); Tetsuhiko Yoshida, Tsukuba (JP)

(73) Assignee: TOAGOSEI CO., LTD., Tokyo (JP)

( * ) Notice: Subject to any disclaimer, the term of this patent is extended or adjusted under 35 U.S.C. 154(b) by 0 days.

(21) Appl. No.: 17/871,833

(22) Filed: Jul. 22, 2022

(65) Prior Publication Data
US 2023/0160876 A1 May 25, 2023

(30) Foreign Application Priority Data
Jul. 28, 2021 (JP) ................. 2021-123580

(51) Int. Cl.
*G01N 33/50* (2006.01)
*A61K 38/10* (2006.01)
*A61K 47/64* (2017.01)
*C07K 7/08* (2006.01)

(52) U.S. Cl.
CPC ......... *G01N 33/5008* (2013.01); *A61K 38/10* (2013.01); *A61K 47/645* (2017.08); *C07K 7/08* (2013.01); *C07K 2319/09* (2013.01)

(58) Field of Classification Search
CPC ...... G01N 33/50; C07K 7/08; C07K 2319/09; C07K 2319/10; A61K 47/645; C12Y 207/11001; C12N 9/12
See application file for complete search history.

(56) References Cited

U.S. PATENT DOCUMENTS

| | | | | |
|---|---|---|---|---|
| 2012/0122210 A1* | 5/2012 | Yoshida | .................. | A61P 25/00 435/325 |
| 2023/0280333 A1* | 9/2023 | Baileykobayashi | ... | A61K 47/50 435/29 |

OTHER PUBLICATIONS

Derakhshankhah, H., & Jafari, S. (2018). Cell penetrating peptides: A Concise review with emphasis on biomedical applications. Biomedicine & Pharmacotherapy, 108, 1090-1096. (Year: 2018).*
Goyal P, Pandey D, Siess W. Phosphorylation-dependent regulation of unique nuclear and nucleolar localization signals of LIM kinase 2 in endothelial cells. J Biol Chem. Sep. 1, 2006;281(35):25223-30. doi: 10.1074/jbc.M603399200. Epub Jul. 4, 2006. PMID: 16820362.
Kobayashi N, Niwa M, Hao Y, Yoshida T. Nucleolar localization signals of LIM kinase 2 function as a cell-penetrating peptide. Protein Pept Lett. Dec. 2010;17(12):1480-8. doi: 10.2174/0929866511009011480. PMID: 20937035.
Extended European Search Report from corresponding EP patent application No. 22187370.6; dated Dec. 15, 2022; 9 pages.

* cited by examiner

*Primary Examiner* — Thea D'Ambrosio
*Assistant Examiner* — Naghmeh Nina Moazzami
(74) *Attorney, Agent, or Firm* — Young Basile Hanlon & MacFarlane, P.C.

(57) ABSTRACT

According to the present disclosure, a technology for efficiently introducing a desired foreign substance from the outside of eukaryotic cells into at least the cytoplasm (and the nucleolus) of the cells is provided. A method disclosed here includes a step of preparing a construct for introducing a foreign substance including a carrier peptide fragment composed of any of amino acid sequences: KKRTLRKKKRKKR (SEQ ID NO: 1), KKRTLRKRRRKKR (SEQ ID NO: 2), KKRTLRKRKRKKR (SEQ ID NO: 3) and KKRTLRKKRRKKR (SEQ ID NO: 4), and a foreign substance that is bound to an N-terminal side and/or C-terminal side of the carrier peptide fragment, a step of supplying the construct for introducing a foreign substance to a sample containing desired eukaryotic cells, and a step of incubating the sample to which the construct for introducing a foreign substance is supplied and introducing the construct into eukaryotic cells in the sample.

8 Claims, 3 Drawing Sheets
Specification includes a Sequence Listing.

SEQUENCE LISTING

```
Sequence total quantity: 5
SEQ ID NO: 1            moltype = AA   length = 13
FEATURE                 Location/Qualifiers
REGION                  1..13
                        note = Synthetic
source                  1..13
                        mol_type = protein
                        organism = synthetic construct
SEQUENCE: 1
KKRTLRKKKR KKR                                                            13

SEQ ID NO: 2            moltype = AA   length = 13
FEATURE                 Location/Qualifiers
REGION                  1..13
                        note = Synthetic
source                  1..13
                        mol_type = protein
                        organism = synthetic construct
SEQUENCE: 2
KKRTLRKRRR KKR                                                            13

SEQ ID NO: 3            moltype = AA   length = 13
FEATURE                 Location/Qualifiers
REGION                  1..13
                        note = Synthetic
source                  1..13
                        mol_type = protein
                        organism = synthetic construct
SEQUENCE: 3
KKRTLRKRKR KKR                                                            13

SEQ ID NO: 4            moltype = AA   length = 13
FEATURE                 Location/Qualifiers
REGION                  1..13
                        note = Synthetic
source                  1..13
                        mol_type = protein
                        organism = synthetic construct
SEQUENCE: 4
KKRTLRKKRR KKR                                                            13

SEQ ID NO: 5            moltype = AA   length = 13
FEATURE                 Location/Qualifiers
REGION                  1..13
                        note = Synthetic
source                  1..13
                        mol_type = protein
                        organism = synthetic construct
SEQUENCE: 5
KKRTLRKNDR KKR                                                            13
```

CARRIER PEPTIDE FRAGMENT FOR NUCLEOLAR LOCALIZATION AND USE THEREOF

CROSS-REFERENCE TO RELATED APPLICATIONS

The present application claims the priority on Japanese Patent Application No. 2021-123580, filed Jul. 28, 2021, the entire contents of which are incorporated herein by reference.

REFERENCE TO SEQUENCE LISTING SUBMITTED VIA EFS-WEB

This application includes an electronically submitted sequence listing in XML format. The XML file contains a sequence listing entitled "KYDO-103-A.xml" which was created on Feb. 5, 2023 and is 7,235 bytes in size. The sequence listing contained in this XML file is part of the specification and is hereby incorporated by reference herein in its entirety.

BACKGROUND

The present disclosure relates to a method of introducing (transferring) a foreign substance from the outside of eukaryotic cells into the cytoplasm (and into the nucleolus) of the cells, and a construct for introducing a foreign substance containing a carrier peptide fragment used in the method.

Conventionally, foreign substances such as polypeptides, and specifically biological active substances, have been introduced into cells (eukaryotic cells) of humans and other mammals to change characteristics of the cells (and tissues and organs composed of the cells) or enhance or improve the functions of the cells. In an example of this technology, a cell penetrating peptide (CPP) is used.

For example, WO 2011/013700 discloses a construct for introducing a foreign substance including an amino acid sequence (carrier peptide fragment) shown in SEQ ID NO 5 known as a nucleolar localization signal (hereinafter referred to "NoLS") of LIM kinase 2 described in Journal of Biological Chemistry, Vol. 281, No. 35, 2006, pp. 25223-25230 and Protein and Peptide Letters, Vol. 17, No. 12, 2010, pp. 1480-1488, and a desired foreign substance. Since the construct includes a carrier peptide fragment having cell membrane permeability, a foreign substance can be introduced into the cytoplasm of eukaryotic cells from the outside of the cells.

SUMMARY

Incidentally, in consideration of medical treatments, in recent years, there has been increasing interest in cell penetrating peptides such as the NoLS, and the development of a technology for more efficiently introducing a foreign substance into desired cells is desired. In addition, in recent years, it has been reported that cancer and various diseases (for example, amyotrophic lateral sclerosis (ALS)) are associated with nucleolus abnormalities, and the interest in the nucleolus has been increasing. Therefore, it is desired to develop a new nucleolus marker and develop a method of transferring a foreign substance to the nucleolus.

Therefore, the present disclosure is made in response to such a request, and an purpose of the present disclosure is to provide a method capable of efficiently introducing a desired foreign substance from the outside of eukaryotic cells into at least the cytoplasm (and into the nucleolus) of the cells. In addition, a purpose of the present disclosure is to provide a construct including a carrier peptide fragment and a foreign substance that can efficiently introduce a desired foreign substance from the outside of eukaryotic cells into the cells.

The inventors attempted to substitute various amino acid residues with the NoLS amino acid sequence shown in SEQ ID NO 5 in order to improve the cell membrane permeability of NoLS of LIM kinase 2 disclosed in the above WO 2011/013700. As a result, they found that, in a mutant in which the 8th asparagine residue and the 9th aspartic acid residue counted from the N-terminal side of the NoLS amino acid sequence shown in SEQ ID NO 5 are substituted with basic amino acid residues (arginine residues or lysine residues), the cell membrane permeability is improved, and the nucleolar migration (localization) is also improved. Surprisingly, these substitutions are not so-called conservative amino acid replacement (for example, sequences in which a basic amino acid residue is substituted with another basic amino acid residue) but substitutions in which the charge of the peptide changes. That is, creating and completing the construct disclosed here took a great deal of trial and error from the inventors.

The method disclosed here is a method of introducing (transferring) a desired foreign substance from the outside of eukaryotic cells (that is, the outside of the cell membrane) (particularly, various animal cells having no cell wall and represented by humans and other mammals) into at least the cytoplasm (and into the nucleolus) of the cells. That is, the method of introducing a foreign substance disclosed here includes:

a step of preparing a construct for introducing a foreign substance including a carrier peptide fragment composed of any one of the following amino acid sequences:

KKRTLRKKKRKKR;  (SEQ ID NO 1)

KKRTLRKRRRKKR;  (SEQ ID NO 2)

KKRTLRKRKRKKR;  (SEQ ID NO 3)
and

KKRTLRKKRRKKR;  (SEQ ID NO 4)
and the desired foreign substance that is bound to an N-terminal side and/or C-terminal side of the carrier peptide fragment;

(2) a step of supplying the construct for introducing a foreign substance to a sample containing desired eukaryotic cells; and (3) a step of incubating the sample to which the construct for introducing a foreign substance is supplied and introducing the construct into eukaryotic cells in the sample.

Here, the "foreign substance" is an inorganic compound or an organic compound that can be directly bound to the N-terminal side or C-terminal side of the carrier peptide fragment or can be indirectly bound thereto via an appropriate linker, and has a molecular size and chemical properties with which it can be introduced into eukaryotic cells.

According to the method of introducing a foreign substance having the above configuration, a construct for introducing a foreign substance constructed by directly binding a desired foreign substance (typically, an organic compound such as a polypeptide, a nucleic acid, a dye, and a drug) to an N-terminal side and/or C-terminal side of the carrier peptide fragment or indirectly binding it thereto via an appropriate linker is supplied (that is, added to living eukaryotic cells) to a sample containing desired eukaryotic cells (for example, a culture product containing the cells), and thus the desired foreign substance can be introduced from the outside of the eukaryotic cells (outside the cell membrane) into the cytoplasm (and into the nucleolus through the nuclear membrane) through the cell membrane with high efficiency.

In a preferable embodiment of the method of introducing a foreign substance disclosed here, the foreign substance is any organic compound selected from the group consisting of a polypeptide, a nucleic acid, a dye and a drug. A construct containing this type of organic compound produced is efficiently introduced into at least a desired cytoplasm.

Here, "polypeptide" refers to a polymer having a structure in which amino acids are bonded by peptide bonds. The polypeptide is not limited in the number of peptide bonds (that is, the number of amino acid residues). That is, polypeptides include those generally called peptides having about 10 or more and less than 300 amino acid residues and those generally called proteins (typically, polymer compounds composed of 300 or more amino acid residues). In this field, polypeptides and proteins are not strictly classified. In this specification, polymers (including oligomers) composed of a plurality of amino acids residues are collectively referred to as polypeptides.

In addition, "nucleic acid" refers to a polymer of nucleotides and includes DNA and RNA. The "nucleic acid" is not limited in the number of bases.

In addition, in another preferable embodiment of the method of introducing a foreign substance disclosed here, the foreign substance is bound to the C-terminal side of the carrier peptide fragment, and an α-amino group of lysine on the N-terminal side of the carrier peptide fragment is acetylated. With such a configuration, the intracellular stability of the construct can be improved and the foreign substance can be more stably retained in the cytoplasm and the nucleolus.

In addition, in another preferable embodiment of the method of introducing a foreign substance disclosed here, the eukaryotic cells into which the construct for introducing a foreign substance is introduced are human or non-human mammal cells.

According to the method disclosed here, the foreign substance can be introduced into the cytoplasm of the human or non-human mammal cells and also into the nucleolus with high efficiency.

In addition, in order to achieve the above purpose, according to the present disclosure, an artificially produced foreign substance introduction construct for introducing (transferring) a desired foreign substance from the outside of eukaryotic cells (that is, outside of the cell membrane) (particularly, various animal cells having no cell wall and represented by humans and other mammals) into at least the cytoplasm (also the nucleolus) of the cells is provided.

That is, the construct for introducing a foreign substance disclosed here includes a carrier peptide fragment composed of any one of the following amino acid sequences:

KKRTLRKKKRKKR; (SEQ ID NO 1)

KKRTLRKRRRKKR; (SEQ ID NO 2)

KKRTLRKRKRKKR; (SEQ ID NO 3)
and

KKRTLRKKRRKKR; (SEQ ID NO 4)
and the desired foreign substance that is bound to an N-terminal side and/or C-terminal side of the carrier peptide fragment.

Since such a construct includes a carrier peptide fragment having high cell membrane permeability, the foreign substance can be efficiently introduced into the cytoplasm (and into the nucleolus) of eukaryotic cells.

In a preferable embodiment of the construct for introducing a foreign substance disclosed here, as described above, the foreign substance is any organic compound selected from the group consisting of a polypeptide, a nucleic acid, a dye and a drug.

In addition, preferably, the foreign substance is bound to the C-terminal side of the carrier peptide fragment, and an α-amino group of lysine on the N-terminal side of the carrier peptide fragment is acetylated.

DETAILED DESCRIPTION

Preferable embodiments of the technology disclosed here will be described below. Components other than those particularly mentioned in this specification (for example, general matters regarding a method of chemically synthesizing peptides, a cell culture technique, preparation of a composition containing peptides and nucleic acids as components, and the like) that are necessary for implementation can be recognized by those skilled in the art as design matters based on the related art in the fields of cell engineering, physiology, medicine, pharmacy, organic chemistry, biochemistry, genetic engineering, protein engineering, molecular biology, genetics and the like.

In addition, the technology disclosed here can be implemented based on content disclosed in this specification and common general technical knowledge in the field. Here, in the following description, in some cases, amino acids are represented by one-letter symbols (but, three-letter symbols in the sequence listing) based on nomenclature for amino acids shown in IUPAC-IUB guidelines. Here, the term "amino acid residue" in this specification includes an N-terminal amino acid and a C-terminal amino acid of a peptide chain unless otherwise specified.

In addition, "synthetic peptide" in this specification refers to a peptide fragment of which a peptide chain alone is not independently and stably present in nature, but it is produced through artificial chemical synthesis or biosynthesis (that is, production based on genetic engineering) and can be stably present in a predetermined composition. Here, the term "peptide" refers to an amino acid polymer having a plurality of peptide bonds, and is not limited in the number of amino acid residues.

Here, the left side of the amino acid sequence described in this specification is always the N-terminal side, and the right side thereof is always the C-terminal side.

The construct for introducing a foreign substance disclosed here includes a carrier peptide fragment and a foreign substance that is bound to the N-terminal side and/or C-terminal side of the carrier peptide fragment.

The carrier peptide fragment disclosed here is a sequence defined (determined) by any one of the following amino acid sequences:

KKRTLRKKKRKKR; (SEQ ID NO 1)

KKRTLRKRRRKKR; (SEQ ID NO 2)

KKRTLRKRKRKKR; (SEQ ID NO 3)
and

KKRTLRKKRRKKR; (SEQ ID NO 4)
and is an amino acid sequence that exhibits cell membrane permeability of eukaryotic cells and also nucleolar localization.

The amino acid sequences shown in SEQ ID NOs 1 to 4 are mutants in which the 8th and 9th amino acids from the N-terminal side of the amino acid sequence known as NoLS of LIM kinase 2 shown in SEQ ID NO 5 are replaced with basic amino acids. It is known that LIM kinase 2 is one of protein kinases that are present in human endothelial cells and involved in intracellular signal transduction, and the 491st to 503rd amino acid sequences function as a nucleolar localization signal (NoLS) (refer to Journal of Biological Chemistry, Vol. 281, No. 35, 2006, pp. 25223-25230 and Protein and Peptide Letters, Vol. 17, No. 12, 2010, pp. 1480-1488).

The amino acid sequence shown in SEQ ID NO 1 is a sequence in which the 8th asparagine residue and the 9th aspartic acid residue of NoLS of LIM kinase 2 are substituted with lysine residues.

The amino acid sequence shown in SEQ ID NO 2 is a sequence in which the 8th asparagine residue and the 9th aspartic acid residue of NoLS of LIM kinase 2 were substituted with arginine residues.

The amino acid sequence shown in SEQ ID NO 3 is a sequence in which the 8th asparagine residue of NoLS of LIM kinase 2 is substituted with an arginine residue and the 9th aspartic acid residue thereof is substituted with a lysine residue.

The amino acid sequence shown in SEQ ID NO 4 is a sequence in which the 8th asparagine residue of NoLS of LIM kinase 2 is substituted with a lysine residue and the 9th aspartic acid residue is substituted with an arginine residue.

The carrier peptide fragment disclosed here is typically the same amino acid sequence as the amino acid sequences shown in SEQ ID NOs 1 to 4 and includes a modified sequence of such an amino acid sequence as long as the cell membrane permeability and nucleolar localization are not impaired. Here, the "modified sequence" is an amino acid sequence (modified amino acid sequence) formed by substituting, deleting and/or adding (inserting) one or several (typically, 2 or 3) amino acid residues. Such slightly modified sequences are included in the "carrier peptide fragment" as a technical idea disclosed here because they can be easily used by those skilled in the art based on information disclosed here.

Typical examples of a modified sequence in this specification include, for example, a sequence formed by a so-called conservative amino acid replacement in which 1, 2 or 3 amino acid residues are conservatively substituted and a sequence in which 1, 2 or 3 amino acid residues are added (inserted) or deleted with respect to a predetermined amino acid sequence. Typical examples of conservative amino acid replacements include, for example, a sequence in which a basic amino acid residue is substituted with another basic amino acid residue (for example, mutual substitution between a lysine residue and an arginine residue) and a sequence in which a hydrophobic amino acid residue is substituted with another hydrophobic amino acid residue (for example, a mutual substitution between a leucine residue, an isoleucine residue, and a valine residue).

In all of the amino acid sequences shown in SEQ ID NOs 1 to 4, 11 amino acid residues among 13 amino acid residues are composed of basic amino acids (arginine and lysine). Conventionally, as a peptide having cell membrane permeability, for example, octaarginine (hereinafter referred to as "R8") composed of only the arginine residue shown in SEQ ID NO 6 is known, but the inventors have confirmed through examination that the cytotoxicity of R8 is relatively high. On the other hand, in the carrier peptide fragment composed of any of the amino acid sequences shown in SEQ ID NOs 1 to 4, the inventors have confirmed through examination that, even if the concentration of the carrier peptide fragment is 100 μM, there is almost no cytotoxicity, and the cytotoxicity is much lower than that of R8. That is, the carrier peptide fragment disclosed here has high cell membrane permeability and nucleolar localization and has significantly low cytotoxicity. Although the details of the mechanism are not clear, in the carrier peptide fragment disclosed here, it is estimated that inclusion of a threonine residue and a leucine residue which are neutral amino acids at the 4th and 5th positions in addition to basic amino acids contributes to reduction of cytotoxicity.

The construct for introducing a foreign substance can be designed and constructed by directly bonding a desired foreign substance to the N-terminal side and/or C-terminal side of the carrier fragment or can be indirectly bound (linked) thereto via an appropriate linker.

The linker is not particularly limited, but may be a peptide linker or a non-peptide linker. Although not particularly limited, the amino acid sequence constituting a peptide linker is preferably an amino acid sequence that does not cause steric hindrance and is flexible. The peptide linker can be, for example, a linker composed of 10 or fewer (more preferably, 1 or more and 5 or fewer, for example, 1, 2, 3, 4, or 5 amino acid residue(s)) amino acid residues containing one or two or more amino acid residues selected from among glycine, alanine, and serine. In addition, β alanine may be used as such a linker. The non-peptide linker is not particularly limited, and for example, an alkyl linker, a polyethylene glycol (PEG) linker, an aminohexanoyl spacer or the like may be used.

The foreign substance contained in the construct for introducing a foreign substance disclosed here is typically an organic compound such as a polypeptide, a nucleic acid, a dye, or a drug. When the foreign substance is a polypeptide, a peptide chain is designed so that it includes an amino acid sequence constituting the polypeptide and an amino acid sequence constituting a carrier peptide fragment, the peptide chain is biosynthesized or chemically synthesized, and thereby a construct for introducing a desired foreign substance can be produced. In addition, organic compounds that function as nucleic acids such as various DNA or RNA, dyes (for example, various fluorescent dye compounds such as FAM and FITC), or drugs (for example, anti-tumor agents including a nucleic acid-based anti-tumor agent such as 5-fluorouracil (5FU) and antiviral agents such as azidothymidine (AZT)) can be directly or indirectly bound to the N-terminal side and/or C-terminal side of the carrier peptide fragment by various conventionally known scientific methods to make a construct for introducing a foreign substance.

Although not particularly limited, functions of the foreign substance may include, for example, promotion of stem cell differentiation induction (stem cell differentiation inducing activity), inhibition of tumor cell proliferation (antitumor activity), inhibition of virus-infected cell proliferation (antiviral activity), and control of proteins and nucleic acids in the nucleolus.

In the construct for introducing a foreign substance, the number of foreign substances bound to the carrier peptide fragment is not particularly limited. That is, one or more foreign substances may be bound to one carrier peptide fragment. Although not particularly limited, for example, a polypeptide, a nucleic acid, a drug or the like may be bound to the N-terminal side of one carrier peptide fragment and a dye may be bound to the C-terminal side. Binding a dye to the carrier peptide fragment is preferable because it is easy to evaluate the efficiency of introducing the construct for introducing a foreign substance into eukaryotic cells and localization in the cells.

Since the construct for introducing a foreign substance disclosed here has high migration to the nucleolus, for example, a construct for introducing a foreign substance containing a dye can be used as a nucleolus marker. Such a construct can be introduced into cells by being added to a culture solution containing eukaryotic cells, and additionally, migration to the nucleolus can be performed with high efficiency. As an example of the related art, a method of analyzing the position of the nucleolus, a method of adding a nucleolus staining solution after a cell membrane permeation treatment (for example, a treatment with a surfactant such as TritonX-100) is performed is widely known. However, the construct disclosed here can be used as a nucleolus marker by a simple method of adding a construct to cultured cells and performing incubation without a cell membrane permeation treatment.

Here, when the foreign substance is a polypeptide, the polypeptide to be adopted (amino acid sequence) is not particularly limited. For example, a substance having a relatively large number of amino acid residues such as a polypeptide or protein having about 100 to 1,000 amino acid residues can be used as the foreign substance.

Typically, a total number of amino acid residues constituting the synthetic peptide produced as a construct for introducing a foreign substance is several to several tens (for example, 10) or more, appropriately 1,000 or less, preferably 600 or less, still more preferably 500 or less, and particularly preferably 300 or less (for example, 10 to 300). Polypeptides with such a length are easily synthesized (biosynthesis and chemical synthesis) and easily used.

Regarding the foreign substance, a mature type or a precursor (including a pro type and a pre-pro type) of a polypeptide involved in functions such as development, differentiation, proliferation, canceration, homeostasis, metabolic regulation, and the like of various cells and tissues (organs) is preferable. In addition, the method of introducing a foreign substance disclosed here can be implemented to clarify functions of polypeptides in cells (in living tissues) by introducing polypeptides whose functions are not known in the related art into the cells.

For example, when eukaryotic cells into which a foreign substance is introduced are stem cells of humans and other mammals, it is preferable to use a mature type or a precursor of a polypeptide having various biological activities involved in induction of differentiation of the stem cells. Here, the "stem cells" include somatic stem cells, embryonic stem cells, and induced pluripotent stem cells (iPS cells). In addition, when eukaryotic cells into which a foreign substance is introduced are cancer cells (tumor cells), it is preferable to use various polypeptides involved in induction of apoptosis of the cancer cells (tumor cells). Alternatively, in this case, it is preferable to use a polypeptide that can prevent cancer cells (tumor cells) from inhibiting functions of an immune monitoring mechanism. In addition, when introduction target eukaryotic cells are bacteria-infected cells or virus-infected cells, it is preferable to use various polypeptides involved in induction of apoptosis of the infected cells, polypeptides that can prevent bacteria or viruses from proliferating in the infected cells, or polypeptides that can prevent bacterial or viral infection from spreading from the infected cells.

Here, like the carrier peptide fragment, the polypeptide as a foreign substance may contain a modified amino acid sequence formed by substituting, deleting and/or adding (inserting) one or several amino acid residues as long as its function is maintained.

In the construct for introducing a foreign substance in which a foreign substance is bound to the C-terminal side of the carrier peptide fragment, it is preferable to acetylate α-amino groups of the amino acid residue on the N-terminal side of the carrier peptide fragment. Specifically, since the amino acid residue on the N-terminal side of the amino acid sequences shown in SEQ ID NOs 1 to 4 is lysine, it is preferable to acetylate α-amino groups of the lysine be. Although the detailed mechanism is unknown, since α-amino groups of amino acids on the N-terminal side are acetylated and modified in most proteins in eukaryotic cells, the intracellular stability of the construct can be improved and the foreign substance can be more stably retained in the cytoplasm and the nucleolus with such a configuration.

In the construct for introducing a foreign substance, it is preferable to amidate the amino acid residue on the C-terminal side. When carboxyl groups of amino acid residues (typically, C-terminal amino acid residues of peptide chains) are amidated, it is possible to improve structural stability (for example, protease resistance) of such a construct in the cytoplasm and the nucleolus. In addition, when carboxyl groups are amidated, since the hydrophilicity of the construct is improved, it is possible to improve the solubility of such a construct in an aqueous solvent. Examples of aqueous solvents include water, various buffer solutions, a saline (for example, PBS), and a cell culture solution.

For example, when a foreign substance is bound to the N-terminal side of the carrier peptide fragment composed of any of the amino acid sequences shown in SEQ ID NOs 1 to 4, it is preferable to amidate carboxyl groups of arginine on the C-terminal side of the carrier peptide fragment. In addition, for example, when the foreign substance is a polypeptide and such a polypeptide is bound to the C-terminal side of the carrier peptide fragment, it is preferable to amidate carboxyl groups of the C-terminal amino acid residue of the polypeptide.

Among the constructs for introducing a foreign substance, those having a relatively short peptide chain (including polypeptides composed as foreign substances, carrier peptide fragments and peptide linkers) can be easily produced according to a general chemical synthesis method. For example, either a conventionally known solid-phase synthesis method or liquid-phase synthesis method may be used. A solid-phase synthesis method in which Boc (t-butyloxycarbonyl) or Fmoc (9-fluorenylmethoxycarbonyl) is applied as a protecting group for an amino group is preferable. That is, according to a solid-phase synthesis method using a commercially available peptide synthesizer, and the peptide chain having a desired amino acid sequence and a modified (N-terminal acetylation, C-terminal amidation, etc.) moiety can be synthesized. Here, only a part of the peptide chain may be synthesized by the method, and for example, a peptide chain containing only a carrier peptide fragment or a carrier peptide fragment and a peptide linker moiety may be synthesized.

Alternatively, peptide moieties may be produced by biosynthesis based on a genetic engineering method. That is, a polynucleotide (typically, DNA) of a nucleotide sequence (including an ATG start codon) that encodes a desired amino acid sequence is synthesized. Then, a recombinant vector having an expression gene construct composed of a synthesized polynucleotide (DNA) and various regulatory elements (including a promoter, a ribosome binding site, a terminator, an enhancer, and various cis elements that control an expression level) for expressing the amino acid sequence in host cells is constructed according to host cells.

According to a general technique, this recombinant vector is introduced into predetermined host cells (for example, yeast, insect cells, and plant cells), and the host cells or tissues or subjects containing the cells are cultured under predetermined conditions. Accordingly, desired peptides can be produced in cells. Then, peptide moieties are isolated from the host cells (in a culture medium if secreted), and as necessary, refolding, purification and the like are performed, and thereby a desired peptide moiety can be obtained.

Here, regarding a method of constructing a recombinant vector, and a method of introducing a constructed recombinant vector into host cells, and the like, methods conventionally performed in the field may be directly used, and such methods themselves do not particularly characterize the technology disclosed here, and thus detailed description thereof will be omitted.

For example, a fusion protein expression system can be used for efficient mass production in host cells. That is, a gene (DNA) that encodes an amino acid sequence of a desired polypeptide is chemically synthesized, and the synthesized gene is introduced into a suitable site of an appropriate fusion protein expression vector (for example, GST (Glutathione S-transferase) fusion protein expression vector such as pET series commercially available from Novogen and pGEX series commercially available from Amersham Biosciences K.K.). Then, host cells (typically, *E. coli*) are transformed with the vector. The obtained transformant is cultured to prepare a desired fusion protein. Then, the protein is extracted and purified. Then, the obtained purified fusion protein is cut with a predetermined enzyme (protease), and released desired peptide fragments (that is, a designed artificial polypeptide) are collected by a method such as affinity chromatography. When such a conventionally known fusion protein expression system (for example, a GST/His system commercially available from Amersham Biosciences K.K. can be used) is used, it is possible to produce a construct for introducing a desired foreign substance (artificial polypeptide).

Alternatively, template DNA (that is, a synthetic gene fragment including a nucleotide sequence that encodes an amino acid sequence of a peptide moiety of a construct for introducing a foreign substance) for a cell-free protein synthesis system may be constructed, various compounds (ATP, RNA polymerase, amino acids, etc.) necessary for peptide moiety synthesis are used, and thus a desired polypeptide can be synthesized in vitro using a so-called cell-free protein synthesis system. Regarding the cell-free protein synthesis system, refer to, for example, the paper written by Shimizu et al. (Shimizu et al., Nature Biotechnology, 19, 751-755(2001)), and the paper written by Madin et al. (Madin et al., Proc. Natl. Acad. Sci. USA, 97(2), 559-564 (2000)). Based on the techniques described in these papers, many companies had already commissioned polypeptides at the time of filing this application, and cell-free protein synthesis kits (for example, commercially available from CellFree Sciences Co., Ltd. Japan) are commercially available.

A single-stranded or double-stranded polynucleotide including a nucleotide sequence that encodes the peptide moiety of the construct for introducing a foreign substance and/or a nucleotide sequence complementary to the sequence can be easily produced (synthesized) by conventionally known methods. That is, when codons corresponding to amino acid residues constituting a designed amino acid sequence are selected, a nucleotide sequence corresponding to the amino acid sequence is easily determined and provided. Then, once the nucleotide sequence is determined, a (single-stranded) polynucleotide corresponding to a desired nucleotide sequence can be easily obtained using a DNA synthesizer or the like. In addition, desired double-stranded DNA can be obtained using the obtained single-stranded DNA as a template according to various enzymatic synthetic techniques (typically, polymerase chain reaction: PCR). In addition, the polynucleotide may be in the form of DNA or in the form of RNA (mRNA, etc.). Double-stranded or single-stranded DNA may be provided. When single-stranded DNA is provided, it may be a coding strand (sense strand) or a non-coding strand (antisense strand) of sequence complementary thereto.

As described above, the polynucleotide obtained in this manner can be used as a material for constructing a recombinant gene (expression cassette) for peptide production in various host cells or in a cell-free protein synthesis system.

The construct for introducing a foreign substance can be suitably used as an effective component of a composition for applications based on the function of the foreign substance. Here, the construct for introducing a foreign substance may be in a salt form as long as the function of the foreign substance is not lost. For example, an acid addition salt obtained by an addition reaction of an inorganic acid or an organic acid that is generally used according to a general method can be used. Therefore, "construct for introducing a foreign substance" described in this specification and the claims includes such salt forms.

The construct for introducing a foreign substance may be provided as a composition that can contain various pharmaceutically (pharmacologically) acceptable carriers according to the usage form in addition to the construct for introducing a foreign substance as an effective component.

Regarding the carrier, for example, carriers that are generally used in the peptide drug as a diluent, an excipient or the like are preferable. The carriers may appropriately vary depending on applications and forms of the construct for introducing a foreign substance, but typically, water, a physiological buffer solution, and various organic solvents may be exemplified. In addition, the carrier may be a non-drying oil such as an aqueous solution containing an alcohol (such as ethanol) with an appropriate concentration, glycerol, an olive oil, or may be a liposome. In addition, examples of a secondary component that can be contained in the pharmaceutical composition include various fillers, extending agents, binders, moisturizers, surfactants, dyes, and fragrances.

The form of the composition is not particularly limited. Examples of typical forms include liquids, suspensions, emulsions, aerosols, foams, granules, powders, tablets, capsules, and ointments. In addition, for use in injection or the like, lyophilizates and granules for preparing a drug solution by performing dissolving in a saline or an appropriate buffer solution (for example, PBS) immediately before use can be prepared.

A process itself of preparing various forms of drug (compositions) including the construct for introducing a foreign substance (main component) and various carriers (secondary component) as materials may be performed according to a conventionally known method, and such a production method itself does not characterize the present disclosure, and thus detailed description thereof will be omitted. Examples of detailed sources of information on prescription include Comprehensive Medicinal Chemistry, edited by Corwin Hansch, published by Pergamon Press (1990).

A method of introducing a construct for introducing a foreign substance in a living organism (in vivo) or outside a living organism (in vitro) using the construct for introducing a foreign substance disclosed here (composition) is provided. The method includes the following steps (1) to (3):

a step of preparing a construct for introducing a foreign substance including a carrier peptide fragment composed of any one of amino acid sequences shown in SEQ ID NOs 1 to 4 and a desired foreign substance that is bound to an N-terminal side and/or C-terminal side of the carrier peptide fragment, a step of supplying the construct for introducing a foreign substance to a sample containing desired eukaryotic cells, and a step of incubating the sample to which the construct for introducing a foreign substance is supplied and introducing the construct into eukaryotic cells in the sample.

The "eukaryotic cells" include, for example, various tissues, internal organs, organs, blood, lymph, and the like in vivo. The "eukaryotic cells" include, for example, various cell masses, tissues, internal organs, organs, blood, and lymph extracted from living bodies, and cell lines and the like in vitro.

The composition containing the construct disclosed here can be used in vivo according to a method and in a dose depending on its form and purpose. For example, only a desired amount of the composition in the form of a liquid can be administered to affected parts (for example, malignant tumor tissues, virus-infected tissues, and inflammatory tissues) of patients (that is, a living organism) through intravenous, intramuscular, subcutaneous, intracutaneous or intraperitoneal injection. Alternatively, a solid form such as a tablet or a gel-like or aqueous jelly-like form such as an ointment can be directly administered to predetermined tissues (that is, for example, an affected part such as tissues and organs including tumor cells, virus-infected cells, inflammatory cells, or the like). Alternatively, a solid form such as a tablet can be administered orally. In the case of oral administration, in order to prevent digestive enzyme decomposition in the gastrointestinal tract, encapsulation or a protective (coating) material is preferably applied.

Alternatively, with respect to eukaryotic cells cultured outside a living organism (in vitro), an appropriate amount of the composition disclosed here (that is, an appropriate amount of the construct for introducing a foreign substance) may be supplied to a culture solution containing desired eukaryotic cells at least once. The amount supplied each time and the number of times it is supplied are not particularly limited because they can vary depending on conditions such as the type of eukaryotic cells to be cultured, the cell density (cell density when the culture starts), the number of passages, culture conditions, and the type of the culture medium. For example, the composition is preferably added once, twice, or more times so that the concentration of the carrier peptide fragment in the culture solution is within a range of about 0.05 µM or more and 100 µM or less, for example, within a range of 0.5 µM or more and 50 µM or less, for example, within a range of 1 µM or more and 20 µM or less, or for example, within a range of 1 µM or more and 10 µM or less. In addition, the incubation time after the construct is added is not particularly limited because it may vary depending on the type of eukaryotic cells and various conditions. For example, it can be 0.5 hours or longer, 1 hour or longer, 4 hours or longer, 8 hours or longer, or 20 hours or longer. Here, incubation conditions may vary depending on the type of eukaryotic cells and are not particularly limited, and for example, incubation ca be performed in a 5% $CO_2$ atmosphere at 37° C.

Here, an example of the in vitro introduction method is shown in the following examples.

A method of evaluating introduction efficiency of the construct for introducing a foreign substance is not particularly limited. For example, when a dye (typically, a fluorescent dye compound) is bound to the construct, the efficiency of introducing into eukaryotic cells can be evaluated using microscopic observation (for example, confocal laser scanning microscopic observation), flow cytometry or the like. In addition, the efficiency of introducing the construct can be evaluated by an immunochemical method (for example, western blotting and immune cell staining) using an antibody that specifically recognizes a peptide moiety of the construct.

Several examples of the technology disclosed here will be described below, and are not intended to limit the technology disclosed here to such specific examples.

Production of Construct for Introducing a Foreign Substance

Five synthetic peptides (Peptides 1 to 5) shown in Table 1 were prepared. Peptides 1 to 5 were peptides composed of amino acid sequences shown in SEQ ID NOs 1 to 5. Among amino acid sequences known as NoLS of LIM kinase 2 shown in SEQ ID NO 5, in all of the amino acid sequences shown in SEQ ID NOs 1 to 4, the 8th and 9th amino acid residues from the N-terminal side were substituted with basic amino acids (arginine or lysine).

All Peptides 1 to 5 were synthesized by performing a solid-phase synthesis method (Fmoc method) using a commercially available peptide synthesizer according to the manual. In addition, Peptides 1 to 5 in which the α-amino groups of lysine on the N-terminal side were all acetylated were synthesized.

Here, since a manner of use of the peptide synthesizer itself does not characterize the technology disclosed here, detailed description thereof will be omitted.

TABLE 1

| Peptide No. | Amino acid sequence | SEQ ID NO |
|---|---|---|
| 1 | KKRTLRKKKRKKR | 1 |
| 2 | KKRTLRKRRRKKR | 2 |
| 3 | KKRTLRKRKRKKR | 3 |
| 4 | KKRTLRKKRRKKR | 4 |
| 5 | KKRTLRKNDRKKR | 5 |

Then, a fluorescent dye FAM($C_{21}H_{12}O_7$: 5(6)-carboxyfluorescein, a molecular weight of 376.3, an excitation wavelength of 495 nm, a fluorescence wavelength of 520 nm) as a foreign substance was directly bound to the amino acid on the C-terminal side of Peptides 1 to 5 based on as general method. Thereby, a construct for introducing a foreign substance containing Peptide 1 (also referred to as "Sample 1"), a construct for introducing a foreign substance containing Peptide 2 (also referred to as "Sample 2"), a construct for introducing a foreign substance containing Peptide 3 (also referred to as "Sample 3"), a construct for introducing a foreign substance containing Peptide 4 (also referred to as "sample 4"), and a construct for introducing a foreign substance containing Peptide 5 (also referred to as "Sample 5") were obtained. Samples 1 to 5 were diluted with DMSO, and sample solutions 1 to 5 having a sample concentration of 2 mM were prepared.

Test 1

Evaluation of Cell Membrane Permeability by Flow Cytometry

HeLa cells (established cell lines derived from human cervical cancer cells) were used as eukaryotic cells, and the cell membrane permeability of Peptides 1 to 5 was analyzed. In this test, as shown in Table 2, the prepared Samples 1 to 5 were used in Examples 1 to 5, and a FAM solution was used as Example 6.

TABLE 2

(SEQ ID NOS: 1 - 5)

| | Configuration of structure (additive) |
|---|---|
| Example 1 | Ac-KKRTLRKKKRKKR-FAM |
| Example 2 | Ac-KKRTLRKRRRKKR-FAM |
| Example 3 | Ac-KKRTLRKRKRKKR-FAM |
| Example 4 | Ac-KKRTLRKKRRKKR-FAM |
| Example 5 | Ac-KKRTLRKNDRKKR-FAM |
| Example 6 | FAM |

Example 1

HeLa cells were cultured in a DMEM (Dulbecco's modified Eagle's medium (Cat No. 043-30085 commercially available from FUJIFILM Wako Pure Chemical Corporation)) containing 10% FBS (fetal bovine serum), which is a general culture medium.

HeLa cells adhered to a culture plate were washed with PBS and a 0.25% trypsin/EDTA solution was then added, and the cells were incubated at 37° C. for 3 minutes. After the incubation, a 10% FBS-containing DMEM was added, trypsin was inactivated, and centrifugation was then performed at 150×g for 5 minutes to precipitate cells. The supernatant generated by centrifugation was removed, and a 10% FBS-containing DMEM was then added to the precipitate (cell pellet) to prepare a cell suspension of about $1\times10^5$ cells/mL. 2 mL of the cell suspension was added to wells of a commercially available 6-well plate (commercially available from AGC Techno Glass Co., Ltd.), and cells were seeded (about $2\times10^5$ cells/well). Then, culturing was performed under 5% $CO_2$ conditions at 37° C. for 2 hours, and cells were adhered to the bottom of the wells.

Then, the 2 mM sample solution 1 was diluted with the 10% FBS-containing DMEM to prepare a sample solution 1 having a concentration of 20 μM of Sample 1. After 1 mL of the culture supernatant was removed from the wells after culturing for 2 hours, 1 mL of the 20 μM sample solution 1 was added to the wells (that is, the concentration of Sample 1 of the culture solution in the well was 10 μM, and the DMSO concentration was 0.5%). Then, cells were incubated under 5% $CO_2$ conditions at 37° C. for 20 hours. After incubation for 20 hours, the culture supernatant was removed from the wells, and the cells in the wells were washed twice with 1 mL PBS. Then, 200 μL of a 0.25% trypsin/EDTA solution was added to the wells, and the cells were incubated at 37° C. for 3 minutes. After the incubation, 400 μL of a 10% FBS-containing DMEM was added to the wells, trypsin was inactivated, the cell suspension in the wells was then transferred to a tube, and the cells were collected. Then, 600 μL of PBS was additionally added to the wells, and the wells were washed. Then, PBS in the wells was transferred to the tube, and thus the cells remaining in the wells were collected in the tube. This tube was centrifuged under conditions of 4° C. and 210×g for 5 minutes. After centrifugation, the supernatant was removed, the precipitate (cell pellet) was suspended (washed) in 1 mL PBS, and centrifugation was then performed under the same conditions as above. After this operation was repeated twice, the supernatant was removed to obtain cells (cell pellets) cultured in the culture medium containing Sample 1.

For the obtained cells (cell pellets), the cell permeability of Sample 1 was analyzed using a flow cytometer. On-Chip Flowcytometer (commercially available from On-Chip Biotechnologies Co., Ltd.) was used as the flow cytometer.

For such analysis, the obtained cell pellets were suspended in 50 μL of PBS. 50 μL of 2×sample buffer for the flow cytometer was additionally added to this suspension, and thereby a cell suspension for analysis was prepared.

Using the flow cytometer, gating was performed based on forward scatter (FSC) and side scatter (SSC), a gate was set for a cell population to be analyzed, and the fluorescent intensity was measured for the cell population within such a gate. Here, analysis was performed so that the cell population was at least 10,000 or more. For measurement of the fluorescent intensity, a fluorescence detector FL2 (optimal detection wavelength of about 543 nm) of the flow cytometer that can detect a fluorescence wavelength of FAM was used. The measurement results were analyzed using commercially available analysis software "FlowJo (registered trademark)" (commercially available from TreeStar) to obtain a mean fluorescent intensity (MFI) of the cell population to be measured.

Example 2

Example 2 was performed in the same manner as in Example 1 except that the prepared sample solution 2 was used in place of the sample solution 1.

Example 3

Example 3 was performed in the same manner as in Example 1 except that the prepared sample solution 3 was used in place of the sample solution 1.

Example 4

Example 4 was performed in the same manner as in Example 1 except that the prepared sample solution 4 was used in place of the sample solution 1.

Example 5

Example 5 was performed in the same manner as in Example 1 except that the prepared sample solution 5 was used in place of the sample solution 1.

Example 6

Example 6 was performed in the same manner as in Example 1 except that a FAM solution diluted with DMSO was used in place of the sample solution 1. Here, the concentration of the FAM solution that was the same as the concentration of the sample solution 1 (that is, the FAM concentration of the culture solution in the well was 10 μM and the DMSO concentration was 0.5%) was used.

Figure 1:
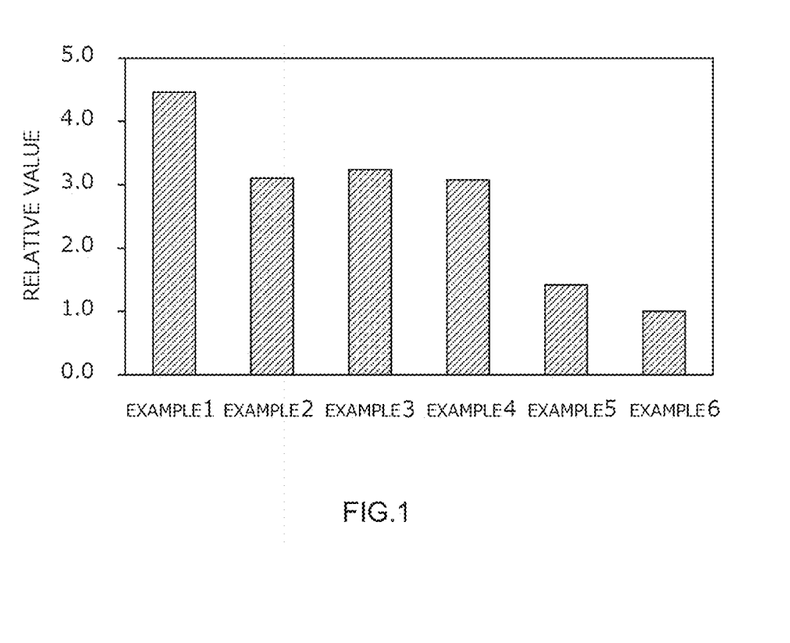
FIG. 1 is a graph showing a relative value (based on 1.0 for Example 6) of an MFI value obtained by analyzing cells after culture by a flow cytometer in tests (Examples 1 to 4) in which a construct for introducing a foreign substance according to one embodiment is added, a test (Example 5) in which a construct including a peptide composed of an amino acid sequence shown in SEQ ID NO 5 is added, and a test (Example 6) in which FAM is added, with respect to HeLa cells culture solution.

FIG. 1 shows the results obtained for Examples 1 to 6. FIG. 1 shows relative values of MFI of respective examples when the MFI value of Example 6 was set to 1.

As shown in FIG. 1, in all of Examples 1 to 5, the MFI value was higher than that of Example 6. Therefore, it can be understood that all of Peptides 1 to 5 had cell membrane permeability. In addition, in all of Examples 1 to 4, the MFI value was more than twice as high as the MFI value of Example 5, and among these, the MFI value of Example 1 was more than three times as high as the MFI value of Example 5. Therefore, it can be understood that Peptides 1 to 4 had better cell membrane permeability than Peptide 5 (NoLS of LIM kinase 2).

In addition, according to the examination by the inventors, it was confirmed that, regardless of whether the foreign substance was not only a fluorescent dye but also any of a polypeptide, a nucleic acid, and a drug, the foreign substance was efficiently introduced from the outside of the cells into the cytoplasm, and also introduced into the nucleolus.

Test 2

In this test, localization of Samples 1 to 5 in HeLa cells was analyzed. HeLa cells were seeded on collagen-coated 8-well slides at about $2 \times 10^4$ cells/well, and cultured overnight in the presence of 5% $CO_2$ at 37° C. A 10% FBS-containing DMEM was used as the cell culture solution. After culturing overnight, the sample solutions 1 to 5 were added to separate wells so that the sample concentration of the culture solution in the wells was 5 μM and the DMSO concentration was 0.5%, and the cells were additionally cultured for 20 hours.

Figure 2A:
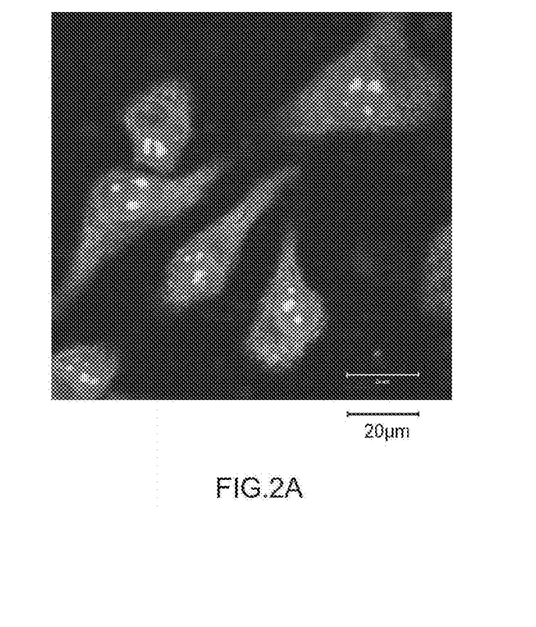
FIG. 2A is an image observed under a confocal laser scanning microscope, which shows intracellular localization of a construct including a carrier peptide fragment composed of an amino acid sequence shown in SEQ ID NO 1.
Figure 2B:
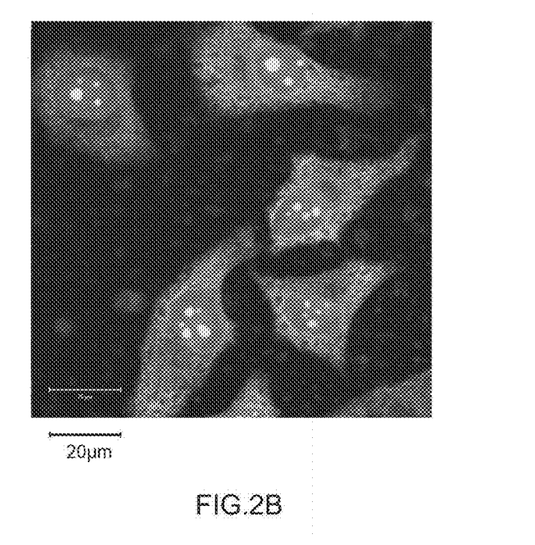
FIG. 2B is an image observed under a confocal laser scanning microscope, which shows intracellular localization of a construct including a carrier peptide fragment composed of an amino acid sequence shown in SEQ ID NO 2.
Figure 2C:
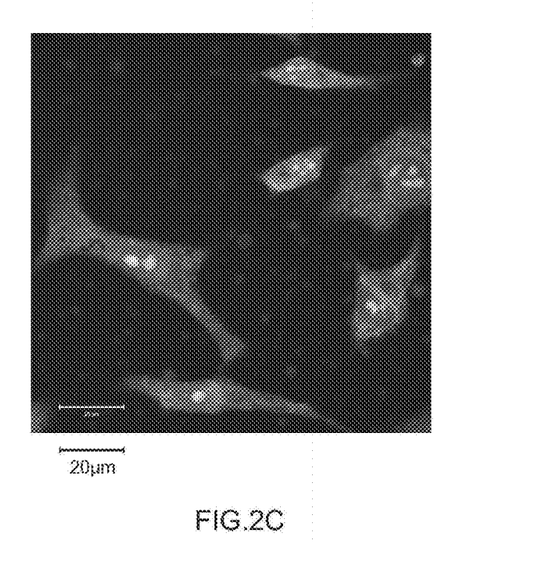
FIG. 2C is an image observed under a confocal laser scanning microscope, which shows intracellular localization of a construct including a carrier peptide fragment composed of an amino acid sequence shown in SEQ ID NO 3.
Figure 2D:
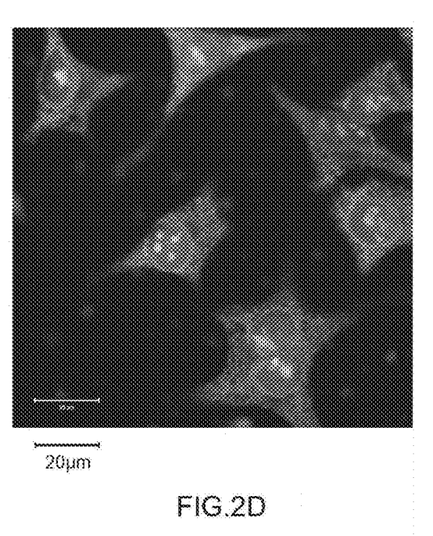
FIG. 2D is an image observed under a confocal laser scanning microscope, which shows intracellular localization of a construct including a carrier peptide fragment composed of an amino acid sequence shown in SEQ ID NO 4.
Figure 2E:
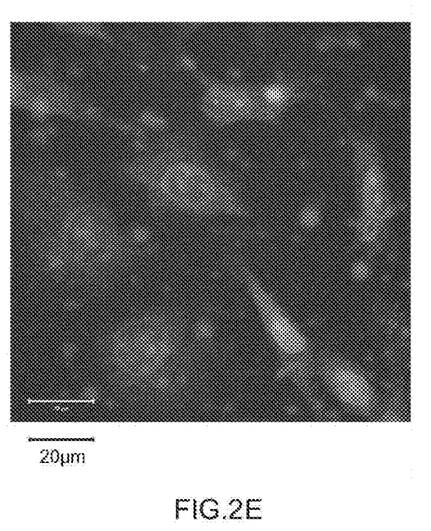
FIG. 2E is an image observed under a confocal laser scanning microscope, which shows intracellular localization of a construct including a carrier peptide fragment composed of an amino acid sequence shown in SEQ ID NO 5.

Then, the supernatant (culture solution) was removed, ice-cooled PBS was added, and washing on ice was performed three times. Then, ice-cooled methanol was added, the sample was left at −20° C. for 10 minutes, and the cells were immobilized. Then, methanol was removed, and washing was then performed three times with ice-cooled PBS. Then, a DAPI-containing encapsulant (commercially available from ThemoFisher Scientific) and a cover glass were used for encapsulation and fluorescence observation was performed under a confocal laser scanning microscope. FIG. 2A shows a fluorescence observation image of an example in which Sample 1 was added, FIG. 2B shows a fluorescence observation image of an example in which Sample 2 was added, FIG. 2C shows a fluorescence observation image of an example in which Sample 3 was added, FIG. 2D shows a fluorescence observation image of an example in which Sample 4 was added, and FIG. 2E shows a fluorescence observation image of an example in which Sample 5 was added. Here, all FIGS. 2A to 2E show images in which fluorescent images of DAPI and FAM were merged.

As clearly understood from FIGS. 2A to 2D, the fluorescence of FAM in Samples 1 to 4 was observed in the nucleolus present in the nucleus of the cells in addition to the cytoplasm. In particular, the fluorescent intensity of FAM in the nucleolus was significantly stronger than that in the cytoplasm, and the contour part of the nucleolus was also clearly observed. On the other hand, as shown in FIG. 2E, the fluorescence of FAM in Sample 5 was slightly observed in the nucleolus, but its fluorescent intensity was weaker than that in FIGS. 2A to 2D, and the contour part of the nucleolus was also unclear. Based on these results, it can be understood that Peptides 1 to 4 had significantly better nucleolar localization than Peptide 5 (NoLS of LIM kinase 2), and a desired foreign substance (here, FAM) could be introduced into the nucleolus.

While specific examples of the technology disclosed here have been described above in detail, these are only examples, and do not limit the scope of the claims. The technologies described in the scope of the claims include various modification and alternations of the above exemplified specific examples.

According to the technology disclosed here, an artificially produced construct for introducing a desired foreign substance from the outside of eukaryotic cells (particularly, various animal cells having no cell wall and represented by humans and other mammals) into at least the cytoplasm and also into the nucleolus is provided. When such a construct is used, it is possible to effectively introduce a desired foreign substance into desired cells and obtain cells into which the foreign substance is introduced and living tissues such as organs including cells containing the foreign substance. In addition, when such a construct is used, it is possible to provide a therapeutic agent for diseases. In addition, since the construct disclosed here has high nucleolar localization, for example, a construct containing a dye can be used as a nucleolus marker. In addition, since the construct disclosed here has significantly low cytotoxicity, and can also introduce a desired foreign substance into the nucleolus, it can be used as a therapeutic agent for cancer and various diseases targeting the nucleolus.

KKRTLRKKKRKKR;  (SEQ ID NO 1)

KKRTLRKRRRKKR;  (SEQ ID NO 2)

KKRTLRKRKRKKR;  (SEQ ID NO 3)
and

KKRTLRKKRRKKR;  (SEQ ID NO 4)
and

What is claimed is:

1. A method of introducing a foreign substance into at least the cytoplasm of eukaryotic cells, comprising:
   a step of preparing a construct for introducing the foreign substance including a carrier peptide fragment composed of any one of the following amino acid sequences:

and the foreign substance that is bound to a N-terminus and/or C-terminus of the carrier peptide fragment;

a step of supplying the construct for introducing the foreign substance to a sample containing eukaryotic cells; and a step of incubating the sample and introducing the construct into eukaryotic cells.

2. The method according to claim 1, wherein the foreign substance is any organic compound selected from the group consisting of a polypeptide, a nucleic acid, a dye and a drug.

3. The method according to claim 1,
wherein the foreign substance is bound to the C-terminus of the carrier peptide fragment, and
wherein an a-amino group of lysine on the N-terminus of the carrier peptide fragment is acetylated.

4. The method according to claim 1, wherein the eukaryotic cells are human or non-human mammal cells.

5. A construct for introducing a foreign substance into at least the cytoplasm of eukaryotic cells, comprising:
a carrier peptide fragment composed of any one of the following amino acid sequences:

```
                            (SEQ ID NO 1)
KKRTLRKKKRKKR;

(SEQ ID NO 2)
KKRTLRKRRRKKR;

(SEQ ID NO 3)
KKRTLRKRKRKKR;
and (SEQ ID NO 4)
KKRTLRKKRRKKR.
```
and
the foreign substance that is bound to an N-terminus and/or C-terminus of the carrier peptide fragment.

6. The construct according to claim 5, wherein the foreign substance is any organic compound selected from the group consisting of a polypeptide, a nucleic acid, a dye, and a drug.

7. The construct according to claim 5,
wherein the foreign substance is bound to the C-terminus of the carrier peptide fragment, and
wherein an α-amino group of lysine on the N-terminus of the carrier peptide fragment is acetylated.

8. A carrier peptide fragment for introducing a foreign substance into at least the cytoplasm of eukaryotic cells, consisting of:
any one of the following amino acid sequences:

```
                            (SEQ ID NO 1)
KKRTLRKKKRKKR;

(SEQ ID NO 2)
KKRTLRKRRRKKR;

(SEQ ID NO 3)
KKRTLRKRKRKKR;
and (SEQ ID NO 4)
KKRTLRKKRRKKR.
```

* * * * *